US00PP10093P

United States Patent [19]

Trees

[11] Patent Number: Plant 0,093

[45] Date of Patent: Oct. 28, 1997

[54] NEW GUINEA IMPATIENS NAMED 'BFP-664 LAVENDER'

[75] Inventor: Scott C. Trees, Arroyo Grande, Calif.

[73] Assignee: Ball Horticultural Company, West Chicago, Ill.

[21] Appl. No.: 670,745

[22] Filed: Jun. 21, 1996

[51] Int. Cl.[6] ..... A01H 5/00

[52] U.S. Cl. ..... Plt./87.6

[58] Field of Search ..... Plt./87.6

*Primary Examiner*—James R Feyrer
*Assistant Examiner*—Kent L. Bell
*Attorney, Agent, or Firm*—Burns, Doane, Swecker & Mathis, L.L.P.

[57] ABSTRACT

A new and distinct New Guinea Impatiens cultivar named 'BFP-664 Lavender' is provided. This new cultivar was the result of a controlled breeding program wherein the 'Tahiti' cultivar (U.S. Plant Pat. No. 8,601) was pollinated by the 'Raspberry Rose' cultivar (U.S. Plant Pat. No. 9,212). The new cultivar forms large dark lavender generally flat flowers with a light eye that display an iridescent appearance. The foliage is medium green in coloration. An attractive compact upright mounded growth habit is exhibited. The new cultivar can be readily distinguished from the 'BFP-661 Purple' cultivar (U.S. Plant Patent application Ser. No. 08/670,744, filed concurrently herewith) that is of the same parentage.

1 Drawing Sheet

SUMMARY OF THE INVENTION

The present invention comprises a new and distinctive Impatiens plant, botanically known as New Guinea Impatiens, and hereinafter is referred to by the cultivar name 'BFP-664 Lavender'.

The new cultivar is the product of a planned breeding program. More specifically, the breeding program which resulted in the production of the new cultivar was carried out in a controlled environment during 1993 at Arroyo Grande, Calif., U.S.A. The female parent (i.e., the seed parent) was the 'Tahiti' cultivar (U.S. Plant Pat. No. 8,601) which exhibits light pink blossoms, dark green foliage, and a compact growth habit. The male parent (i.e., the pollen parent) was the 'Raspberry Rose' cultivar (U.S. Plant Pat. No. 9,212) which exhibits large dark rose blooms with a white eye, medium green foliage, and a moderate growth habit. The parentage of the new cultivar can be summarized as follows:

'Tahiti'×'Raspberry Rose'.

The seeds resulting from the above pollination were sown and plantlets were obtained which were physically and biologically different from each other. Selective study resulted in the identification of a single plant of the new cultivar. This plant initially was designated BFP-664.

It was found that the new cultivar of the present invention:

(a) exhibits attractive large dark lavender flowers with a light eye,
(b) forms medium green foliage,
(c) exhibits a good basal branching character, and
(d) exhibits a compact upright mounded growth habit.

The intense lavender coloration of the flowers contrasts well with the medium green foliage. Plants of the new cultivar can be grown close together in the greenhouse.

Asexual reproduction of the new cultivar by terminal or stem cuttings taken during 1994, at Arroyo Grande, Calif., U.S.A. has demonstrated that the characteristics of the new cultivar as herein described are firmly fixed and are retained through successive generations of such asexual propagation.

The 'BFP-664 Lavender' cultivar has not been observed under all possible environmental conditions to date. Accordingly, it is possible that the phenotype may vary somewhat with variations in the environment, such as temperature, light intensity, and day length.

When the new cultivar of the present invention is compared to the 'BFP-661 Purple' cultivar (U.S. Plant Patent application Ser. No. 08/670,744), filed concurrently herewith, it is found that the new cultivar exhibits a slightly more compact growth habit and smaller flowers.

Plants of the new cultivar are marketed under the Celebrette trademark by the Ball Horticultural Company.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of The Royal Horticultural Society, London, England. The plants were produced from cuttings taken from stock plants of the new cultivar and were transplanted during early November into 10 cm. (4 inch pots) and were grown in a soilless growth medium under standard greenhouse conditions at West Chicago, Ill., U.S.A. The greenhouse temperature was maintained at approximately 72° F. during the day and approximately 65° F. during the night. The plants were in flower eight to nine weeks later when the observations described hereafter were taken.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Basal branching.

*Habit of growth.*—Compact, upright, and mounded. A mature plant commonly measures approximately 6 to 9 cm. in height and approximately 13 to 19 cm. in width. This compares to a height of approximately 6.5 to 8 cm. and a width of approximately 18 to 19 cm. for the 'BFP-661 Purple' cultivar.

*Foliage.*—The configuration is elliptic with an acuminate apex and an acuminate base. The mature leaves of the new cultivar measure approximately 7.5 to 8 cm. in length ×approximately 3 to 3.6 cm. in maximal width compared to approximately 7.2 to 8.5 cm. in length ×approximately 3 to 3.6 cm. in maximal width for the 'BFP-661 Purple' cultivar. The leaf margins are serrate (as illustrated). The mature foliage of new cultivar is Green Group 139A (adaxial), and Yellow-Green Group 148B with a pale red midvein (abaxial). This compares to Green Group 139A (adaxial) and Greyed-Green Group 191A (abaxial) for the 'BFP-661 Purple' cultivar. The stem coloration is Red Group 53B which can be compared to Green Group 137D for the 'BFP-661 Purple' cultivar.

Flower description:

*Flowering habit.*—Freely flowering.

*Natural flowering season.*—Throughout the year in a greenhouse environment.

*Flowers borne.*—Above foliage, arising from leaf axils.

*Flower color.*—The superior petal is pure Purple Group 78A. The lower four petals are Purple Group 78A, the two lateral petals have attachment points of Red-Purple Group 73C, and the two inferior petals have attachment points of Purple Group 78D (adaxial), and Purple-Violet Group 80C (abaxial). This compares to somewhat bluer than Red-Purple Group 74A and brighter and redder than Purple-Violet Group 80A with the four lower petals having bases of Red Group 53C producing an eye (adaxial), and Purple-Violet Group 80C (abaxial).

*Quantity of flowers.*—Approximately 4 to 7 per axil which can be compared to 4 to 5 per axil for the 'BFP-661 Purple' cultivar.

*Number of petals.*—Five, and overlapping.

*Petal Shape.*—Heart-shaped, with the upper three petals having broader bases than the lower two petals.

*Flower size.*—Approximately 6.2 to 6.7 cm. in length and approximately 6.1 to 6.5 cm. in width. This can be compared to approximately 5.7 to 6 cm. in length and approximately 5.7 to 6 cm. in width for the 'BFP-661 Purple' cultivar.

*Flower buds.*—Ellipsoidal in configuration, and generally covered with three sepals plus two rudimentary sepals fused into the under surface of the superior petal. A spur originating from the base of the inferior sepal is approximately 5.8 to 6 cm. in length on fully opened flowers which can be compared to approximately 4 to 4.6 cm. for the spur length of the 'BFP-661 Purple' cultivar. The spur coloration is Red Group 53B which can be compared to Red-Purple Group 63A for the 'BFP-661 Purple' cultivar.

*Reproductive organs.*—The stamens are Red Group 42A which can be compared to the generally colorless stamens of the 'BFP-661 Purple' cultivar. The anthers tend to be fused together forming one organ that surrounds the pistil. Commonly the anthers shed pollen prior to the stigma becoming receptive. The pollen coloration is Yellow-Orange Group 15D and the ovary coloration is Yellow-Green Group 146B. This can be compared to a pollen coloration of Yellow-Orange Group 19C and an ovary coloration of Green Group 141A for the 'BFP-661 Purple' cultivar.

I claim:

1. A new and distinct cultivar of New Guinea Impatiens plant named 'BFP-664 Lavender', substantially as herein shown and described, which:

(a) exhibits attractive large dark lavender flowers with a light eye,
(b) forms medium green foliage,
(c) exhibits a good basal branching character, and
(d) exhibits a compact upright mounded growth habit.

* * * * *

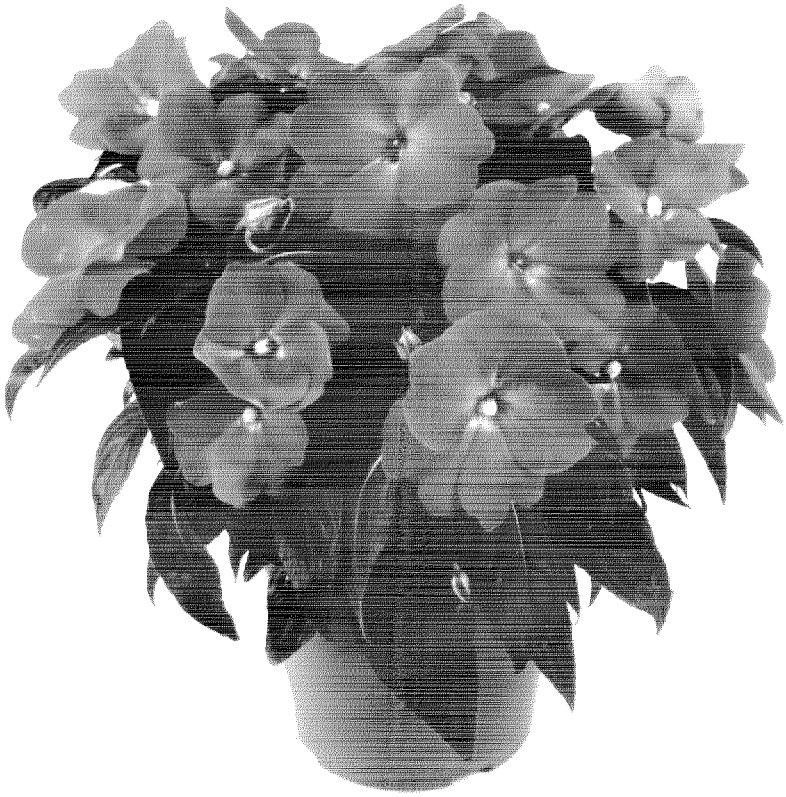

UNITED STATES PATENT AND TRADEMARK OFFICE

CERTIFICATE OF CORRECTION

PATENT NO. : Plant 10,093

DATED : October 28, 1997

INVENTOR(S) : Scott C. Trees

It is certified that error appears in the above-identified patent and that said Letters Patent is hereby corrected as shown below:

ON THE TITLE PAGE:

In Section [11], change "0,093" to --10,093--.

In the header above columns 3 and 4, change "0,093" to --10,093--.

Signed and Sealed this

Fourteenth Day of April, 1998

Bruce Lehman

*Attest:*

BRUCE LEHMAN

*Attesting Officer*

*Commissioner of Patents and Trademarks*